United States Patent
Hancock et al.

(10) Patent No.: US 6,610,077 B1
(45) Date of Patent: Aug. 26, 2003

(54) EXPANDABLE EMBOLI FILTER AND THROMBECTOMY DEVICE

(75) Inventors: David Hancock, deceased, late of San Francisco, CA (US), by Katherine Hancock, executor; William Stephen Tremulis, Redwood City, CA (US); Saypin Phonthalasa, San Francisco, CA (US); Olin Palmer, Mountain View, CA (US); Larry Voss, San Jose, CA (US); Gary A. Walker, Fremont, CA (US)

(73) Assignee: Endovascular Technologies, Inc., Menlo Park, CA (US)

(*) Notice: Subject to any disclaimer, the term of this patent is extended or adjusted under 35 U.S.C. 154(b) by 83 days.

(21) Appl. No.: 09/768,653

(22) Filed: Jan. 23, 2001

(51) Int. Cl.⁷ .............................................. A61M 29/00
(52) U.S. Cl. ........................................ 606/200; 606/194
(58) Field of Search ................................ 606/191, 194, 606/198, 200, 151, 108; 604/96, 104–107

(56) References Cited

U.S. PATENT DOCUMENTS

| | | |
|---|---|---|
| 3,996,938 A | 12/1976 | Clark, III |
| 5,171,233 A | 12/1992 | Amplatz et al. |
| 5,190,555 A | 3/1993 | Wetter et al. |
| 5,192,286 A | 3/1993 | Phan et al. |
| 5,234,439 A | 8/1993 | Wilk et al. |
| 5,329,942 A | 7/1994 | Gunther et al. |
| 5,352,184 A | 10/1994 | Goldberg et al. |
| 5,354,310 A | 10/1994 | Garnic et al. |
| 5,449,372 A | 9/1995 | Schmaltz et al. |
| 5,643,281 A | 7/1997 | Suhocki et al. |
| 5,720,754 A | 2/1998 | Middleman et al. |
| 5,749,883 A | 5/1998 | Halpern |
| 5,769,816 A | 6/1998 | Barbut et al. |
| 5,792,156 A | 8/1998 | Perouse |
| 5,846,260 A | 12/1998 | Maahs |
| 5,848,964 A | 12/1998 | Samuels |
| 5,941,896 A * | 8/1999 | Kerr ............................ 606/200 |
| 6,171,328 B1 * | 1/2001 | Addis .......................... 606/200 |
| 6,179,861 B1 * | 1/2001 | Khosravi et al. ........... 606/200 |

* cited by examiner

Primary Examiner—Gloria M. Hale
(74) Attorney, Agent, or Firm—Fulwider Patton Lee & Utecht, LLP (57) ABSTRACT

Expandable emboli filter and thrombectomy devices adapted for use with microcatheters to remove debris from blood vessels. The devices embody expanded profiles that span the entirety of various sized target vessels and thus are particularly effective in the engagement of debris found in vessels.

27 Claims, 5 Drawing Sheets

EXPANDABLE EMBOLI FILTER AND THROMBECTOMY DEVICE

BACKGROUND OF THE INVENTION

The present invention relates generally to filtering and thrombectomy devices and systems which can be used to capture embolic material or thrombi found in blood vessels. The filtering devices and systems of the present invention are particularly useful when performing balloon angioplasty, stenting procedures, laser angioplasty or atherectomy in critical vessels where the release of embolic debris into the bloodstream can occlude the flow of oxygenated blood to the brain or other vital organs, which can cause devastating consequences to the patient. The thrombectomy devices are suited for the removal of thrombus in a variety of vessels. While the embolic filtering and thrombectomy devices and systems of the present invention are particularly useful in the cerebral vasculature and neurovasculature, the inventions can be used in conjunction with any vascular interventional procedure in which there is an embolic risk.

A variety of non-surgical interventional procedures have been developed over the years for opening stenosed or occluded blood vessels in a patient caused by the build up of plaque or other substances on the wall of the blood vessel. Such procedures usually involve the percutaneous introduction of the interventional device into the lumen of the artery, usually through a catheter. In typical PTA procedures, a guiding catheter or sheath is percutaneously introduced into the cardiovascular system of a patient through the femoral artery and advanced to near the target vasculature. A guidewire and a dilatation catheter having a balloon on the distal end are introduced through the guiding catheter with the guidewire sliding within the dilatation catheter. The guidewire is first advanced out of the guiding catheter into the patient's vasculature and is directed across the arterial lesion. The dilatation catheter is subsequently advanced over the previously advanced guidewire until the dilatation balloon is properly positioned across the arterial lesion. Once in position across the lesion, the expandable balloon is inflated to a predetermined size with a radiopaque liquid at relatively high pressures to radially expand the atherosclerotic plaque of the lesion and thereby dilate the lumen of the artery. The balloon is then deflated to a small profile so that the dilatation catheter can be withdrawn from the patient's vasculature and the blood flow resumed through the dilated artery. As should be appreciated by those skilled in the art, while the above-described procedure is typical, it is not the only method used in angioplasty. Another procedure is laser angioplasty which utilizes a laser to ablate the stenosis by super heating and vaporizing the deposited plaque. Atherectomy is yet another method of treating a stenosed blood vessel in which cutting blades are rotated to shave the deposited plaque from the arterial wall. A vacuum catheter is usually used to capture the shaved plaque or thrombus from the blood stream during this procedure.

In the procedures of the kind referenced above, abrupt reclosure may occur or restenosis of the artery may develop over time, which may require another angioplasty procedure, a surgical bypass operation, or some other method of repairing or strengthening the area. To reduce the likelihood of the occurrence of abrupt reclosure and to strengthen the area, a physician can implant an intravascular prosthesis for maintaining vascular patency, commonly known as a stent, inside the artery across the lesion. The stent is crimped tightly onto the balloon portion of the catheter and transported in its delivery diameter through the patient's vasculature. At the deployment site, the stent is expanded to a larger diameter, often by inflating the balloon portion of the catheter.

Prior art stents typically fall into two general categories of construction. The first type of stent is expandable upon application of a controlled force, as described above, through the inflation of the balloon portion of a dilatation catheter which, upon inflation of the balloon or other expansion means, expands the stent to a larger diameter to be left in place within the artery at the target site. The second type of stent is a self-expanding stent formed from, for example, shape memory metals or super-elastic nickel-titanium (NiTi) alloys, which will automatically expand from a compressed state when the stent is advanced out of the distal end of the delivery catheter into the body lumen. Such stents manufactured from expandable heat sensitive materials allow for phase transformations of the material to occur, resulting in the expansion and contraction of the stent.

The above minimally invasive interventional procedures, when successful, avoid the necessity of major surgical operations. However, there is one common problem which can become associated with all of these types of procedures, namely, the potential release of embolic debris into the bloodstream that can occlude distal vasculature and cause significant health problems to the patient. For example, during deployment of a stent, it is possible that the metal struts of the stent can cut into the stenosis and shear off pieces of plaque which become embolic debris that can travel downstream and lodge somewhere in the patient's vascular system. Pieces of plaque material can sometimes dislodge from the stenosis during a balloon angioplasty procedure and become released into the bloodstream. Additionally, while complete vaporization of plaque is the intended goal during a laser angioplasty procedure, quite often particles are not fully vaporized and thus enter the bloodstream. Likewise, not all of the emboli created during an atherectomy procedure may be drawn into the vacuum catheter and, as a result, enter the bloodstream as well.

When any of the above-described procedures are performed in the vessels supplying blood to the brain, the release of emboli into the circulatory system can be extremely dangerous and sometimes fatal to the patient. Naturally occurring debris can also be highly dangerous to a patient. That is, debris which travels through the blood vessel as a natural result of bodily functions or disease states and not as a result of an intervention procedure. Debris that is carried by the bloodstream to distal vessels of the brain can cause these cerebral vessels to occlude, resulting in a stroke, and in some cases, death. Therefore, although cerebral percutaneous transluminal angioplasty has been performed in the past, the number of procedures performed has been limited due to the justifiable fear of causing an embolic stroke should embolic debris enter the bloodstream and block vital downstream blood passages.

Medical devices have been developed to attempt to deal with the problem created when debris or fragments that naturally occur or that enter the circulatory system following vessel treatment utilizing any one of the above-identified procedures. One approach which has been attempted is the cutting of any debris into minute sizes which are unlikely to occlude major vessels within the patient's vasculature. However, it is often difficult to control the size of the fragments which are formed, and the potential risk of vessel occlusion still exists, making such a procedure in the carotid arteries a high-risk proposition.

Other techniques which have been developed to address the problem of removing embolic debris include the use of catheters with a vacuum source which provides temporary suction to remove embolic debris from the bloodstream. However, as mentioned above, there have been complications with such systems since the vacuum catheter may not always remove all of the embolic material from the bloodstream, and a powerful suction could injure the patient's vasculature or remove more blood than is safe. Other techniques which have had some limited success include the placement of a filter or trap downstream from the treatment site to capture embolic debris before it reaches the smaller blood vessels downstream. However, there have been problems associated with conventional filtering systems. In particular, certain previously developed filtering devices do not optimize the area for embolic collection. That is, conventional filtering devices may not present a collection device that spans the entity of the vessel or it may include supporting structure that itself impedes emboli collection. Certain other devices are not effective when used in conjunction with a microcatheter.

Moreover, thrombectomy and foreign matter removal devices have been disclosed in the art. However, such devices have been found to have structures which are either highly complex or lacking in sufficient or effective expansion and retraction capabilities. Disadvantages associated with the devices having highly complex structure include difficulty in manufacturability as well as use in conjunction with microcatheters. Other less complex devices can pull through clots due to in part the lack of experience in using the same, or lack an adequately fine mesh for capturing clots or foreign bodies.

Furthermore, systems heretofore disclosed in the art are generally limited by size compatibility and the increase in vessel size as the emboli is drawn out from the distal vascular occlusion location to a more proximal location. If the thrombectomy device is too large for the vessel it will not deploy correctly to capture the clot or foreign body, and if too small in diameter it cannot capture thromboembolic material or foreign bodies across the entire cross section of the blood vessel. Thus, a thrombectomy device that can be expanded to a relatively large diameter from a relatively small diameter is desirable as is the ability to effectively control such expansion and contraction.

What has been needed is a reliable filtering or thrombectomy device and system for use when treating blood vessels. The filter devices should be capable of filtering any naturally occurring embolic debris or that which may be released into the bloodstream during an interventional treatment, while minimizing the area occupied by structure supporting the filter so as to minimally obstruct blood flow, and safely contain the debris until the filtering device is removed from the patient's vasculature. The thrombectomy devices should embody an expanded profile that completely occupies the vessel at the repair site as well as structure for effectively expanding and retracting the device. Moreover, such devices should be relatively easy to deliver through a microcatheter, as well as be deployed and removed from the patient's vasculature and also should be capable of being used in narrow and very distal vasculature such as the cerebral vasculature. The following invention addresses these needs.

SUMMARY OF THE INVENTION

Briefly and in general terms, the present invention is directed toward expandable devices for repairing blood vessels. The expandable devices are particularly suited for removing emboli or thrombi from the bloodstream of a human or animal. One significant advantage provided by the present invention is the potential use of the expandable devices in narrow and very distal vasculature.

In one aspect of the invention, there is provided a loop with an embolic filter attached thereto. The loop is configured to self-expand generally perpendicularly to and optionally offset to a longitudinal axis of a delivery catheter. A tether is provided to effect the deployment from and withdrawal into the delivery catheter. The self-expandable loop and filter structure advantageously expands to occupy the entire cross-section of the lumen into which it is deployed. When the device is in its expanded configuration, the shape of the loop is defined by the lumen and the tether is positioned near a wall of the lumen.

In another aspect, the present invention includes multiple loops that are connected by longitudinally extending fibers. The connecting fibers may be crossing or non-crossing and may terminate at a superior loop or continue distally to define a tapered distal end. A catheter is provided for deploying the double loop device as is a tether which effectuates the delivery and withdrawal of the device. The multiple loops are intended to self-expand to occupy the entirety of the cross-section of the blood vessel into which it is deployed, the loops assuming the geometry of the vessel. Additionally, when the device is in its expanded configuration, the tether is intended to generally lie adjacent a wall defining the lumen thereby accomplishing less blood flow obstruction. The distal loops may also provide internal support for an embolic filter, facilitating material entry into the filter.

In a third aspect of the invention, an embolectomy snare is provided which has the advantage of being able to assume a very small profile when packed within a delivery catheter. The embolectomy snare is characterized by including a basket that is formed from non-overlapping elongate members.

In a fourth aspect of the invention, improved expansion control and a means for optimizing expansion profiles is incorporated into a thrombectomy device. In particular, one or more stops are provided on an elongate member to cause a basket-like thrombectomy device configured coaxially about the elongate member to thereby open and close the basket. By varying the weave pattern of the basket of the thrombectomy device, upon expansion of the same, a concavity can be formed, the same being particularly useful for engaging and removing clots from a blood vessel.

These and other objects and advantages of the invention will become apparent from the following more detailed description, when taken in conjunction with the accompanying drawings of illustrative embodiments.

DETAILED DESCRIPTION OF THE PREFERRED EMBODIMENTS

Figure 1A:
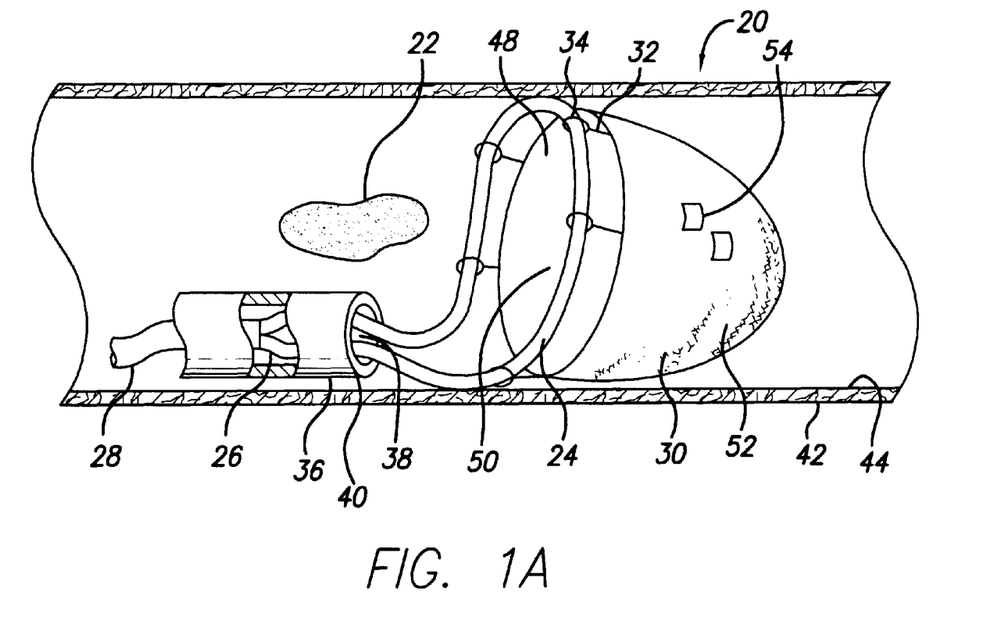
FIG. 1A is a perspective view, partially in cross-section, of an expandable device of the present invention in its deployed configuration.

Turning now to the drawings, and particularly to FIG. 1A, there is shown an expandable device 20 of the present invention. The expandable device 20 is suited for repairing vessels and in particular, for capturing emboli 22 found in the bloodstream of a patient. Due to its novel structure, the repair device 20 embodies an expanded profile that is highly effective in filtering unwanted material from vasculature and is capable of being deployed within very narrow and distal vasculature, including the cerebral vasculature.

Figure 1B:
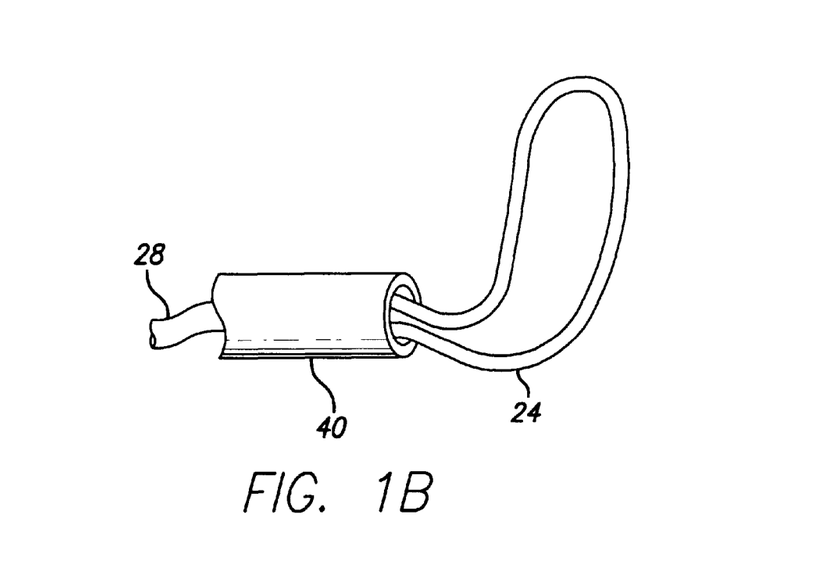
FIG. 1B is a perspective view, depicting a loop and an expandable device that is integral with an elongate member.

In one presently preferred embodiment, the expandable device 20 includes a loop 24 attached by conventional means to a distal end 26 of an elongate member 28. Attached to the loop 24 is an emboli filter 30. The loop 24 can be soldered to the elongate member 28 or can be affixed thereto using epoxy or other forms of adhesive. Alternatively, the loop 24 can be an integral part of the elongate member 28 (See FIG. 1B). A band or other mechanical fixation devices (not shown) could also be used for this purpose. The emboli filter 30 could be attached to the loop 24 using a plurality of proximally extending anchors or fibers 32, each of which are configured into small hoops 34 that engage the loop member 24.

An elongate, tubular catheter 36, preferably a microcatheter or otherwise a lumen of a conventional stent delivery catheter, is also provided. The microcatheter 36 includes an internal bore 38 that is adapted to coaxially and slidably receive the elongate member 28 as well as the looped member 24 and emboli filter 30 assembly. The delivery catheter 36 is capable of being manipulated independent of the elongate member 28 and loop/filter assembly, for example, by holding the delivery catheter 36 in a particular longitudinal position while advancing the elongate member 28. Alternatively, the delivery catheter 36 can be withdrawn or advanced while maintaining a desired longitudinal position of the elongate member 28.

The loop 24 is preferably made from a looped length of superelastic wire. The elongate member 28 can be formed from a guide wire.

Significantly, the loop 24 is configured so that when it exits the distal end 40 of the delivery catheter 36, the loop 24 projects generally perpendicularly to longitudinal axes of the elongate member 28 and catheter 36. It is also contemplated, that for particular purposes, the loop 24 could project at an acute or obtuse angle respecting the elongate member 28. Accordingly, it is contemplated that the loop 24 also embodies shape retaining material and a material that permits the loop 24 to quickly and repeatedly return to a desirable pre-formed shape.

It is also highly significant that the loop 24 embodies sufficient flexibility so that upon ejection from the delivery catheter 36, the loop 24 generally conforms to an inside circumference of a blood vessel 42 into which it is deployed. In doing so, the elongate member 28 and distal portion 40 of the delivery catheter 36 are generally positioned adjacent walls 44 defining an interior lumen of the blood vessel 42. Thus, the expandable loop 24 spans the entirety of the circumference of the vessel 42. Moreover, the elongate member 28 and delivery catheter 36 are advantageously displaced from the center or median of the bloodflow, such that debris traveling through the vessel can avoid these components and must pass through the loop 24.

Figure 2A:
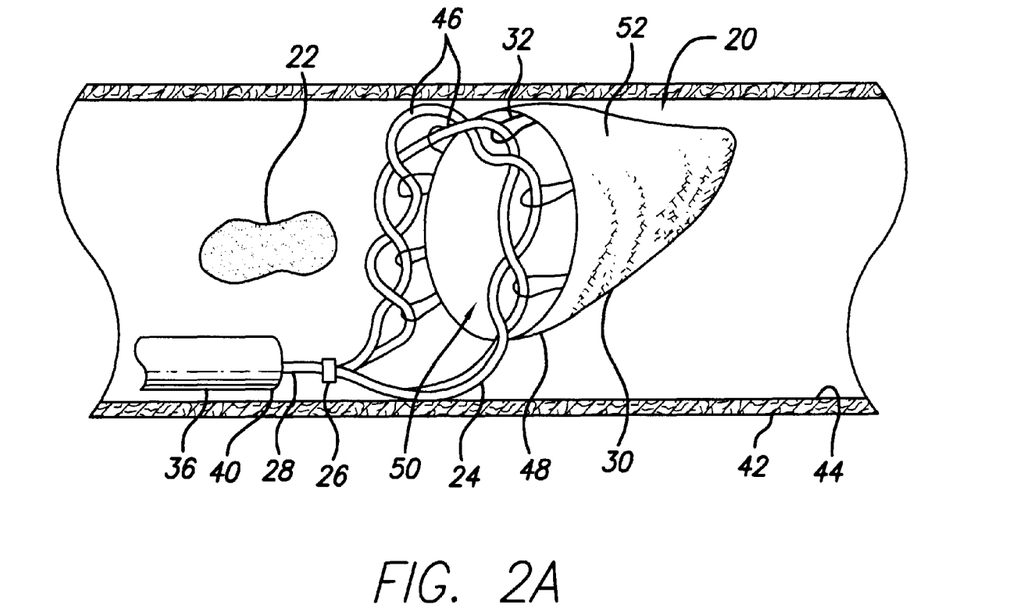
FIG. 2A is a perspective view, partially in cross-section, of an alternate embodiment of the present invention in its deployed configuration.
Figure 2B:
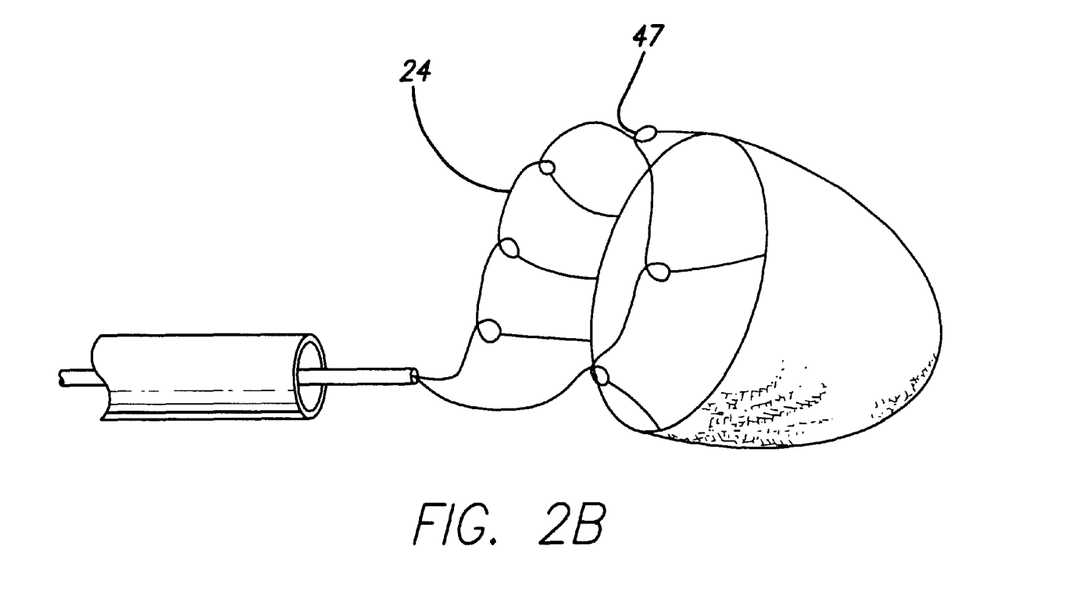
FIG. 2B is a perspective view, depicting a loop configured with mini-loops for spacing tethers.

In an alternative embodiment (FIG. 2A), the loop 24 can embody a plurality of members 46, preferably two such members, entwined about each other. The twined configuration 46 advantageously embodies additional hoop strength without sacrificing the other advantages of the loop configuration such as the ability to assume the contour of the interior 44 of the blood vessel 42. The twined configuration also provides structure for maintaining a desired spacing between anchors or fibers 32 which are used to attach the filter 32 to the loop 24. Further, rather than relying on an interference fit between the hoops 34 and the loop 24 to accomplished desired spacing, the anchors 32 can embody single mini-loops which encircle one of the twined members 46. In yet another aspect of the invention, the loop 24 can embody mini-loops 47 that serve to correctly space the tethers 32 (See FIG. 2B).

The filter 30 includes a proximally directed opening 48 to an interior 50. The body 52 of the filter 30 can have any exterior profile but it is preferred that its exterior generally assume a hemispherical or conical shape. The fully expanded filter 30 has an opening 48 to the body 52 that is generally circular but can be modified for a particular application. In one preferred embodiment, the body 52 is made from a mesh-fabric material through which blood can readily flow. The mesh contains apertures or pores 54 through which the blood passes but which are small enough so that debris does not flow therethrough. Alternatively, the filter can embody laser cut mylar or is defined by ultrasonically welded polymer fibers. In yet another aspect, the fiber crossing can be bonded with flexible adhesive.

The filter sub-assembly 30 can be made from surgical mesh or alternatively the filter 30 can embody a network of braided members or fibers. For example, the filter can embody a braided expansion wire 50. In one presently preferred embodiment, the expandable device 20 consists of an elongate member 28 or guidewire with a metal braided basket (not shown) attached to a loop or otherwise directly attached to a superior end of the wire.

Figure 3:
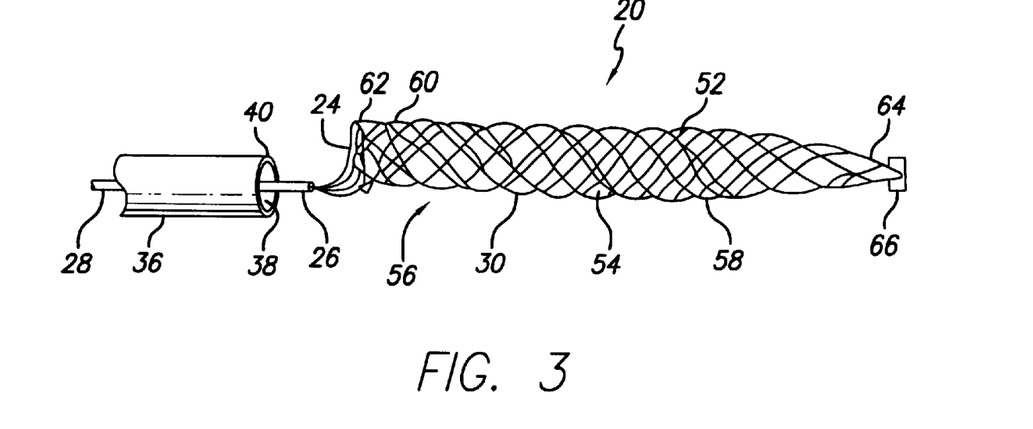
FIG. 3 is a perspective view of another embodiment of an expandable device of the present invention in its expanded configuration.

It is additionally contemplated that, as shown in FIG. 3, the weaved basket 56 may be formed from polypropylene suture 58. In order to manufacture the weaved basket 56, the polypropylene suture 58 is wrapped in an over and under weaving pattern about a mandrel (not shown) which can embody a tapered or straight cylindrical profile. A proximal or inferior end portion 60 includes reversals of direction 62. A distal or superior end portion 64 is tied to form a closed structure. The tied end is cut to provide an even profile and a polymide tube 66 having the smallest diameter possible is placed about the closed end. Thereafter, an adhesive is applied to retain the polymide tubing 66 on the braided basket 56.

A shape set loop 24 is then threaded through the reversals 62. By doing so, the braided basket 56 is fixed to the loop 24. In a presently preferred embodiment, the polypropylene suture 58 has a diameter of 0.003 inches, the polymide tubing 66 has an inner diameter of 0.0318 inches and an outer diameter of 0.0364 inches, and the loop 24 is formed from 0.003 inch diameter nickel titanium wire.

It is contemplated that in one preferred embodiment the braided basket 56 comprises an 8-strand pattern that results in a closed net. The length of the basket 56 will vary depending on the size of the material to be removed. The diameter of the basket 56 will also vary from 2 mm to 50 mm depending on the lumen diameter of the vessel from which material is to be removed. The basket 56 is attached to a loop 24 which opens the proximal end of the basket 56, allowing entry of material into the basket 56. The loop 24 may be formed of a variety of elastic 24 or superelastic materials. The diameter of the loop 24 will match that of the basket 56. The loop 24 may be covered, in part or in full, with a platinum coil to minimize the potentiality of trauma caused by the device, and/or to enhance attachment of the basket 56 to the loop 24. The inner diameter of this coil corresponds to the outer diameter of the loop strand, allowing for clearance. A typical coil is 0.009 inches in inner diameter with a wire diameter of 0.0025 inches. The loop 24 is attached to the elongate member 28 via soldering and other joining technology.

The expandable devices 20 advantageously embody a simple structure that can assume a very small contracted profile. Thus, the device can be used in conjunction with a flexible microcatheter 36 that can traverse very narrow, tortuous and distal vasculature. Upon expansion, the self-expanding loop 24 assumes the contour of the vessel into which it is deployed thereby providing an optimized structure for capturing debris. Moreover, when the loop 24 is expanded, the microcatheter 36 and elongate member 28 lie adjacent a wall defining vessel and substantially out of the way of the flow path. Accordingly, the expandable device 20 can be used to effectively repair virtually any portion of a patient's vasculature by simply modifying the range of expanded loop 24 sizes.

Figure 4A:
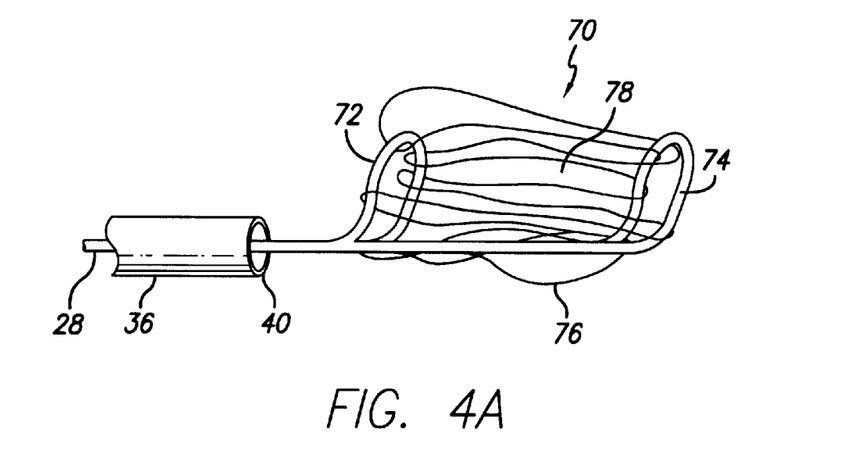
FIG. 4A is a perspective view of yet another embodiment of an expandable device of the present invention in its expanded configuration.

Referring now to FIG. 4A, another preferred embodiment of an expandable device is shown. In this embodiment, the present invention is embodied in a dual-looped, expandable device 70. The dual-looped device includes a first or inferior self expanding loop 72, a second or superior expanding loop 74, each of which are attached to a distal end of an elongate member or wire 28. Highly flexible connecting fibers 76 are routed between the first 72 and second 74 loops to thereby define an emboli receiving cavity 78 when the device is in its expanded configuration. The connecting fibers 76 act as structure for engaging and capturing emboli and can be cross or non-crossing. Additionally, the connecting fibers 76 may embody a single continuous fiber or may include multiple fibers. The fibers may be tied to the second loop 74 or they can extend (not shown) beyond the second loop 74, tapering off and terminating with a pointed end.

In one preferred embodiment of the dual looped device 70, the elongate member 28 is comprised of Nitinol and includes a 0.004 inch outer diameter reduced section for receiving portions of the loops 72, 74. Platinum coils (not shown) are employed to accomplish affixing via soldering or similar means, the loops 72, 74 to the elongate member 28. The connecting fibers 76 comprise polypropylene strands. Further, in a preferred embodiment, the connecting fibers 76 are routed such that there are five (5) points of connection per loop 72, 74, however, few or as many as 10 or more points of connection are contemplated.

Figure 4B:
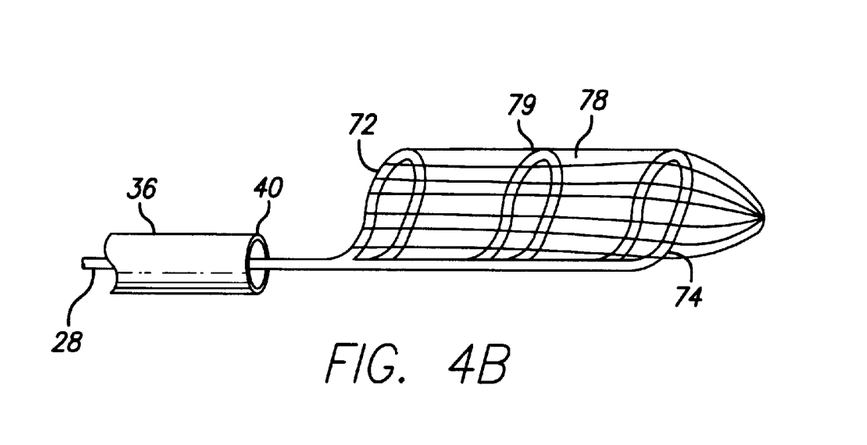
FIG. 4B is a perspective view, depicting an expandable device of the present invention with a medical loop.

The dual-looped device 70 is also contemplated to be used with a generally tubular delivery catheter that is adapted to slidably receive the elongate member 28 as well as receive compressed loops 72, 74. The dual-loop device 70 also embodies the advantages associated with the single loop design. That is, the loops 72, 74 self-expand to assume the entire contour of a blood vessel into which it is employed in such a manner that the delivery catheter 36 and elongate member 28 lie adjacent to the vessel wall that is substantially out of the flow path. FIG. 4B depicts another preferred embodiment in which an additional loop 79 between loops 72 and 74 provides support for the filaments, enhancing entry of material to an interior defined by the device.

In use, the expandable devices depicted in FIGS. 1–4 are contemplated to be packed in a compressed state within the tubular delivery catheter 36. Access is gained to the patient's vasculature via conventional methods and the delivery catheter/expandable device assembly is placed within the patient's vasculature. The assembly is then advanced through the patient's vasculature to a repair site and the distal end 40 of the delivery catheter 36 is positioned beyond the repair site. Thereafter, the expandable device 20, 70 is translated longitudinally with respect to the delivery catheter 36 so that the expandable device exits the distal end of the delivery catheter 36, which in turn, allows the expandable device 20, 70 to self-expand.

As the expandable device 20, 70 expands, it projects at a generally perpendicular angle (though any angle is possible) with respect to the elongate member 28 and the loop 24 or loops 72, 74 assume the contour of the interior of the vessel of lumen. Moreover, the filter body 52 is opened by the expansion of the loop 24 and in the case of the dual-looped device 70, the expansion of the loops 72, 74 facilitate the formation of the embolic receiving cavity 78.

Once it is in its fully deployed configuration, the expandable devices 20, 70 are capable of capturing emboli or other debris traveling antegrade in the bloodstream. The debris enters an opening to the filter body 52 or the emboli receiving cavity 76 and is captured therein. Once the debris is captured, the expandable device 20, 70 may be removed from the vasculature, or other means such as a suction device can be employed to independently first remove the debris and thereafter, the expandable device can be withdrawn.

Figure 5A:
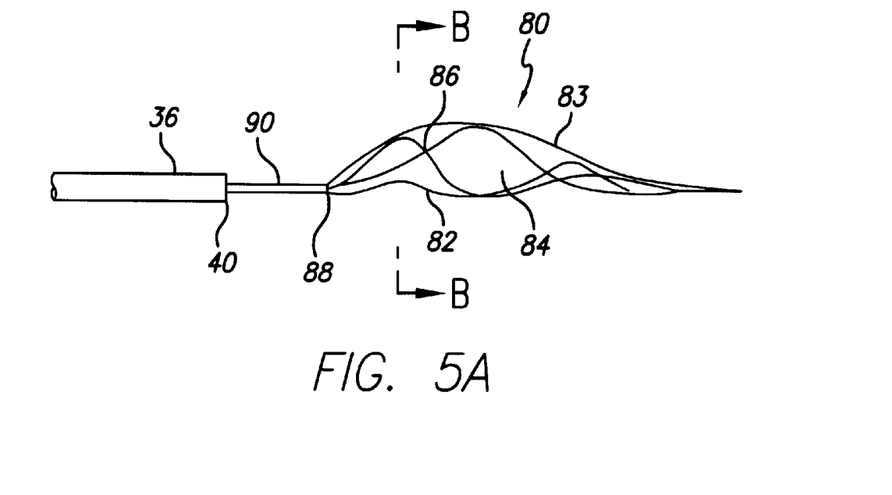
FIG. 5A is a side view of an emboli snare of the present invention shown in its expandable state.
Figure 5B:
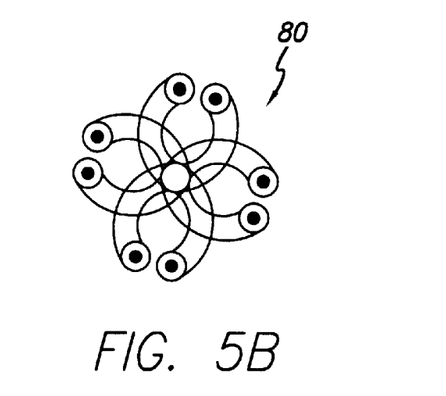
FIG. 5B is a cross-sectional view taken along B—B of the device shown in FIG. 5A.

With reference to FIG. 5A, there is shown another embodiment of an expandable device of the present invention which is specifically adapted for use as an embolectomy snare device 80. The snare device 80 includes a plurality of shape memory elements 82 that are configured in alternating and generally undulating sections to form a basket structure which defines an interior pocket 84 and a proximally directed opening thereto (See FIG. 5B). Adjacent elements 82 on one side of the generally conical, basket-like profile may be laser welded or fixed to each other at points of proximity. A proximal end 88 of the shaped memory elements 82 is affixed by conventional means to an elongate member 90. Further, the snare device 80 is contemplated to be used in conjunction with a generally tubular delivery catheter 36 which is adapted to slidably receive the elongate member 90 as well as the basket 83 in a compressed configuration.

Figure 6:
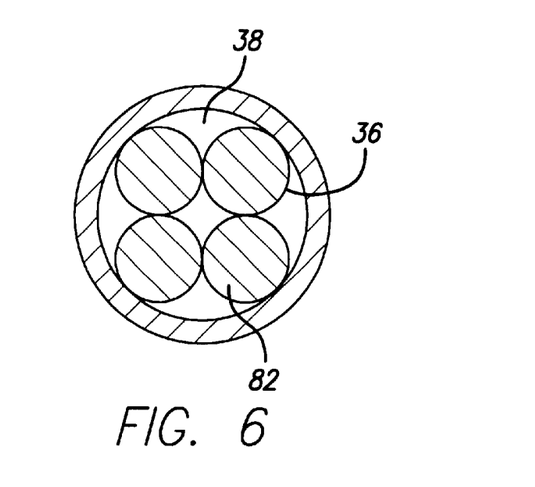
FIG. 6 is a cross-sectional view of the device depicted in FIG. 5A when withdrawn within a delivery catheter.

The snare device 80 advantageously embodies elements which are non-overlapping. To wit, snare device 80 can be packed very tightly within an interior 38 of the delivery catheter 36 such as a microcatheter. This feature is shown in FIG. 6, which depicts a cross-sectional view of a snare device loaded within the delivery catheter 36. Due to its ability to be packed into a very small diameter microcatheter, the snare device 80 is well-suited for use in narrow and distal vasculature.

In use, the snare device 80 is placed in its compressed state within a delivery catheter 38 that is advanced within vasculature to a repair site. The snare device 80 is then ejected from a distal end 40 of the delivery catheter 36 and permitted to self-expand within the target vessel. The expanded snare device 80 is then brought into engagement with embolic material found in the bloodstream. The pocket defined by the basket profile 83 then receives and captures the embolic material, which is then capable of being removed from a patient's vasculature.

It is also to be recognized, however, that the devices described herein can also be delivered through a guidewire lumen of a balloon or stent catheter. This allows for direct placement without requiring the use of a micro-catheter.

Turning now to FIGS. 7–10, there is shown an expandable device 100 which concludes an actuating basket 102 defined by elements 103. The elements 103 are weaved together in a generally helical fashion. Although this expandable basket device 100 is primarily intended for use in thrombectomy procedures, the device has applications to the capture of emboli in the bloodstream as well. The basket device 100 can be used in conjunction with a microcatheter (not shown) or it can be deployed within vasculature without using a microcatheter. As shown in the figures, the basket device 100 may be attached to a distal end 104 of an elongate, tubular carrier 106.

A retainer 108 is provided at a distal end 110 of the basket device 100. The retainer 108 has a generally cylindrical profile and includes an internal bore (not shown). The retainer 108 functions to maintain the distal end 110 of the basket device in a closed configuration both when the basket 100 is unexpanded and when it is expanded.

The basket device assembly device 100 is adapted to be slidably placed about an elongate member 112 in a coaxial arrangement. The elongate member 112 is likewise received in the retainer 108 in a coaxial arrangement. Elongate member 112 includes a plurality of beads 114, the outer profile which is greater than the internal bore of the retainer 108 but smaller than an internal diameter of the elongate tubular member 106.

Figure 7:
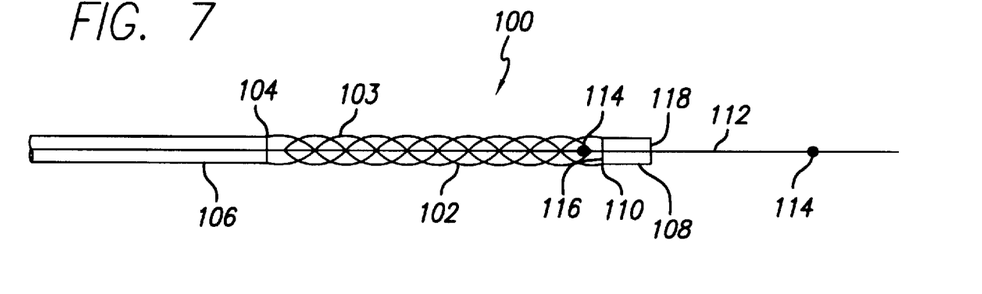
FIG. 7 is a side view of a thrombectomy device of the present invention shown in its fully contracted configuration.
Figure 8:
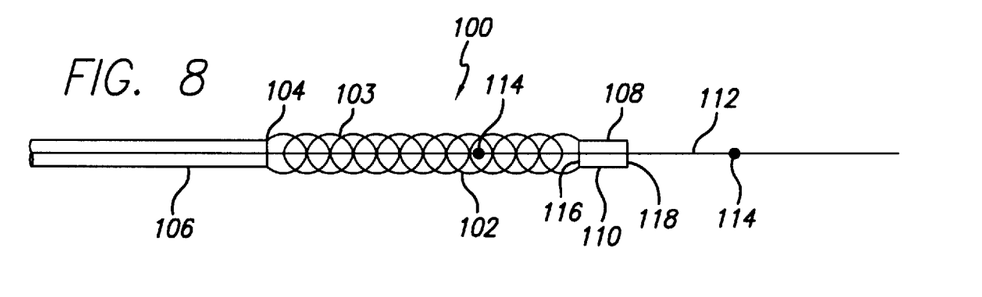
FIG. 8 is a side view of the device depicted in FIG. 7 advanced distally with respect to an elongate member.
Figure 9:
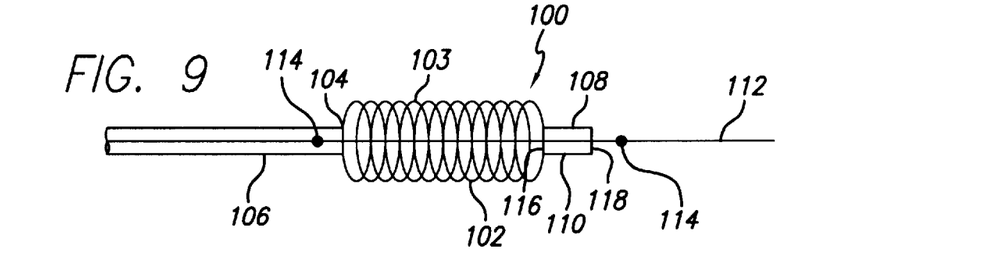
FIG. 9 is a side view of the device depicted in FIG. 8 which is further advanced distally and placed in an expanded configuration.
Figure 10:
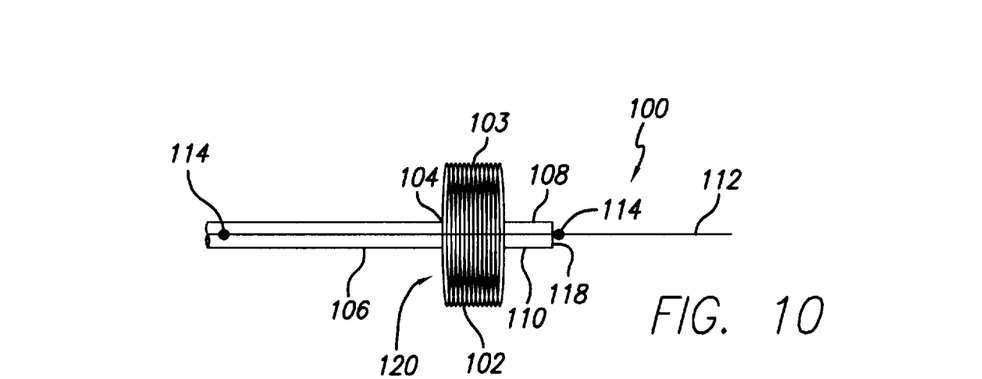
FIG. 10 is a side view of the device depicted in FIG. 9 in its fully expanded configuration.

The beads 114 have a dual function. A proximally positioned bead 114 is employed, as shown in FIG. 7 to retain the basket device 100 in a compressed configuration by holding the proximal bead 114 in engagement with a proximal side 116 with a retainer 108. Expansion of the basket device 100 is achieved by translating the basket device 100 distally with respect to the elongate member 112 and by causing the distal side 118 of the retainer 108 to engage a distally positioned bead 114, the further the basket device 100 is translated distally, the greater the radial expansion. Accordingly, the basket device 100 can be controllably and repeatedly expanded and contracted to the extent desired to engage vessel walls of varied diameters. It is contemplated that the basket device 100 embody wire elements 102 which have more stiff distal portions than proximal portions so that when the basket continues to expand, a concavity 120 is formed. Alternatively, the concavity 120 can be formed if the basket device 100 is leashed to the elongate tubular member, for example.

As stated, the basket device 100 can also be used in combination with the microcatheter. In a first step of use, the microcatheter is employed to deliver an elongate wire 112 which includes only a single bead 114. The microcatheter is then completely withdrawn from a patient's vasculature and a basket device 100 is threaded over the elongate member 112. Once the retainer 108 of the basket device 100 is advanced sufficiently to engage the bead 114, the basket device 100 can be made to expand radially outwardly. In the event use of a microcatheter is essential to the specific application, this alternative approach allows for the use of a basket device 100 with an elongate tubular member that has a larger outer diameter than an inner diameter of the microcatheter, which advantageously allows for increased pushability and column strength on the elements 103 defining the basket portion 102.

In view of the foregoing, it is clear that the expandable devices of the present invention are useful for the repair of vasculature. In particular, the disclosed expandable devices are particularly useful for the capture of emboli as well as for use in thrombectomy procedures.

It will be apparent from the foregoing that, while particular forms of the invention have been illustrated and described, various modifications can be made without departing from the spirit and scope of the invention. Accordingly, it is not intended that the invention be limited, except by the appended claims.

What is claimed is:

1. An expandable device for treating blood vessels, comprising:
   an elongate member having a distal end portion;
   a loop formed from a member entwined about itself or at least two members entwined about each other to form a twined configuration; the loop affixed to the distal end portion; and
   a filter device, the filter device affixed to the loop.

2. The expandable device of claim 1, wherein the twined configuration is formed from a single member.

3. The expandable device of claim 1, wherein the twined configuration is formed from a plurality of members.

4. The expandable device of claim 1, the filter device further comprising a plurality of mini-loops, the mini-loops adapted for receiving a portion of the loop.

5. The expandable device of claim 1, the filter device further comprising a plurality of proximally extending members, the proximally extending members adapted for receiving at least a portion of the loop.

6. The expandable device of claim 1, wherein the filter device has a generally conical profile with a hollow interior and a proximally directed opening to the hollow interior.

7. The expandable device of claim 1, the filter device further includes a plurality of apertures.

8. The expandable device of claim 1, wherein the filter device embodies a surgical mesh material.

9. The expandable device of claim 1, wherein the filter device is defined by a helical mesh pattern.

10. The expandable device of claim 1, the expandable device configured coaxially and slidably within a generally tubular delivery catheter in a compressed state.

11. The expandable device of claim 1, wherein the filter device embodies laser cut mylar.

12. The expandable device of claim 1, wherein the filter is defined at least in part by ultrasonically welded polymer fibers.

13. The expandable device of claim 1, wherein the filter is defined by fiber crossings that are bonded together by a flexible adhesive.

14. The expandable device of claim 10, wherein the loop is self-expanding.

15. The expandable device of claim 14, wherein the loop expands at a generally perpendicular angle to the elongate member when deployed from the delivery catheter.

16. An expandable device for repairing blood vessels, comprising:

an elongate member having a distal end portion;

a first loop and a second loop, each of the first and second loops being affixed to the distal end portion of the elongate member, the second loop being distal to the first loop; and a plurality of connecting fibers extending between the first and second loop.

17. An expandable device for repairing blood vessels, comprising:

an elongate member having a distal end portion;

a first loop and a second loop, each of the first and second loops being affixed to the distal end portion of the elongate member, the second loop being distal to the first loop; and a plurality of connecting members extending between the first and second loop; wherein the connecting members comprise a single member routed between the first and second loops.

18. The expandable device of claim 17, further comprising:

a delivery catheter, the delivery catheter being generally elongate and including an internal bore, the delivery catheter adapted to receive the elongate member and the first and second loops within the bore.

19. An expandable device for repairing blood vessels, comprising:

an elongate member having a distal end portion;

a first loop and a second loop, each of the first and second loops being affixed to the distal end portion of the elongate member, the second loop being distal to the first loop;

a third loop configured between the first and second loops, the third loop adapted to provide medial support; and a plurality of connecting members extending between the first and second loop.

20. The expandable device of claim 18, wherein the first and second loops are self-expanding.

21. The expandable device of claim 20, wherein the first and second loops expand at a generally perpendicular angle to the elongate member.

22. An expandable device for repairing a blood vessel, comprising:

an elongate member having a first stop and a second stop positioned distal to the first stop;

a generally tubular elongate member positioned coaxially about the elongate member and the stops, the tubular elongate member having a distal end portion;

an expandable basket affixed to the distal end portion, the basket having a terminal end; and a slidable member positioned about the elongate member and between the first and second stops, the slidable member affixed to the terminal end;

wherein the slidable member and the tubular elongate member are separate whereby the slidable member and tubular elongate member are displaceable relative to one another so as to increase or decrease the diameter of the basket.

23. The expandable device of claim 22, wherein the slidable member has a first end and a second end, the expandable basket being held in a compressed configuration when the first end is held in contact with the first stop.

24. The expandable device of claim 22, wherein the basket is expanded when the second end is caused to engage the second stop.

25. An expandable device for repairing a blood vessel, comprising:

an elongate member having a first stop and a second stop positioned distal to the first stop;

a generally tubular elongate member positioned coaxially about the elongate member and the stops, the tubular elongate member having a distal end portion;

an expandable basket affixed to the distal end portion, the basket having a terminal end; and a slidable member positioned about the elongate member and between the first and second stops, the slidable member affixed to the terminal end;

wherein the basket is defined by helically routed wire elements, the wire elements having proximal and distal portions, the distal portions being more stiff than the proximal portions.

26. The expandable device of claim 25, herein continued expansion of the basket results in a proximally directed concavity.

27. The expandable device of claim 25, further including at least one leash routed from the basket to the generally tubular elongate member.

* * * * *

UNITED STATES PATENT AND TRADEMARK OFFICE
CERTIFICATE OF CORRECTION

PATENT NO.     : 6,610,077 B1
DATED          : August 26, 2003
INVENTOR(S)    : David Hancock et al.

It is certified that error appears in the above-identified patent and that said Letters Patent is hereby corrected as shown below:

Column 10,
Line 32, after "configuration", change ";" (semicolon), to -- , -- (comma).

Signed and Sealed this

Fourteenth Day of October, 2003

JAMES E. ROGAN
*Director of the United States Patent and Trademark Office*